United States Patent
Bernstein

(10) Patent No.: US 8,106,096 B2
(45) Date of Patent: Jan. 31, 2012

(54) COMPOSITIONS AND METHODS FOR TREATMENT OF OPTIC NERVE DISEASES

(75) Inventor: Steven L Bernstein, Chevy Chase, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 314 days.

(21) Appl. No.: 12/402,833

(22) Filed: Mar. 12, 2009

(65) Prior Publication Data

US 2009/0233862 A1    Sep. 17, 2009

Related U.S. Application Data

(60) Provisional application No. 61/069,118, filed on Mar. 12, 2008.

(51) Int. Cl.
*A61K 31/5575*    (2006.01)
(52) U.S. Cl. .......................................................... 514/573
(58) Field of Classification Search .................... None
See application file for complete search history.

*Primary Examiner* — Christine J Saoud
*Assistant Examiner* — Jon M Lockard
(74) *Attorney, Agent, or Firm* — Morgan, Lewis & Bockius LLP

(57) ABSTRACT

The present invention provides a method for treating or reducing damage to the optic nerve in a subject comprising administering to the subject a therapeutically effective amount of prostaglandin J2 alone or in combination with an effective amount of GM-CSF. In particular aspects of the invention, the subject is a mammal, and in further aspects the mammal is a human.

6 Claims, 3 Drawing Sheets

COMPOSITIONS AND METHODS FOR TREATMENT OF OPTIC NERVE DISEASES

CROSS REFERENCE TO RELATED APPLICATIONS

This application claims the benefit of application Ser. No. 61/069,118, filed Mar. 12, 2008, the disclosure of which is hereby incorporated by reference in its entirety.

STATEMENT OF FEDERALLY SPONSORED RESEARCH AND DEVELOPMENT

This invention was made with government support under NIH Grant No. EY015304 awarded by the National Institutes of Health. The US Government has certain rights in the invention.

INTRODUCTION

Blockage of the blood supply to the part of the optic nerve within the eye can lead to death or dysfunction of optic nerve cells and is called ischemic optic neuropathy. At least two types of ischemic optic neuropathy can occur, which include non-arteritic and arteritic. Non-arteritic ischemic optic neuropathy (NAION), is the most common cause of sudden optic nerve (ON)-related vision loss. NAION affects about 6,000 Americans every year. These individuals typically wake up with severe vision loss in one eye. Importantly, ~20% of individuals with an NAION event suffer another event in the contralateral eye (Newman et al., 2002, Am. J. Opthalmol. 134, 317-328).

Like other ischemic neuropathies, NAION is associated with multiple factors, including hypertension, cataract extraction, diabetes and sleep apnea (Palombi et al., 2006, Br J. Opthalmol. 2006 July; 90(7):879-82. Epub 2006 Mar. 23; McCulley, 2001, Opthalmology 108(7):1275-8; IONDT study group, 1996, Arch. Opthalmol 114, 1366-1374).

A clinical examination almost always reveals ON edema, visible as a bulging optic nerve disk (intra-ocular ON edema). ON edema gradually resolves over 5-7 weeks, with optic nerve atrophy and pallor, and the majority of affected individuals show altitudinal visual field defects (Hattenhauer et al., 1997, Am. J. Opthalmol. 123, 103-107). There are no effective options currently available for preserving post-stroke function. However, well controlled studies document partial visual recovery from NAION in a significant percentage (~30%) of patients (IONDT study group, 2000, Arch. Opthalmol. 118, 793-798), but the reasons for this are not known. This demonstrates that improved treatments are needed.

Following NAION, blindness occurs from at least 2 major causes including: 1) retinal ganglion cell (RGC) neuronal and glial cell death (Hayreh, S. S., 1974, Br. J. Opthalmol. 58, 955-963; Chauhan et al., 2004, Invest. Opthalmol. 45, 144-152; Bernstein et al., 2003, Invest. Opthalmol Vis. Sci. 44, 4153-4162; Goldenberg-Cohen et al., 2005, Invest. Opthalmol. Vis. Sci. 46, 2716-2725), and 2) ON scarring resulting in RGC-higher CNS disconnection associated with failure of RGC axonal regrowth (Knox et al., 2000, Trans Am. Opthalmol. Soc. 98, 203; Bernstein et al., 2003, supra). The latter is important since some RGCs remain alive even after optic nerve transection (Berkelaar et al., 1994, J. Neurosci. 14, 4368-4374; Selles-Navarro et al., 2001, Exp. Neurol. 167, 282-289). ON scarring from a variety of causes has been shown to block later attempts at remyelination and reconnection (Selles-Navarro et al., 2001, supra; Chauhan, 2004, supra).

RGCs are typical long-axon CNS neurons, so identifying therapies to reduce post-NAION damage is relevant to axonal ischemic infarct and optic nerve stroke specifically.

Isolated CNS-white matter ischemia is actually a common disorder, but has only recently been identified as a major cause of morbidity (Schmidt et al., 2002, Cerebrovasc. Dis. 13, 16-20; Basile et al., 2006, Cerebrovasc. Dis. 21, 315-322). This clinical problem has been exacerbated by the lack of models for this condition, and has only recently begun to be addressed (Matthews, 2004, Stroke 35, 92-93; Frost et al., 2006, Behav. Brain Res. 169, 206-211). Because of this problem, few studies of isolated in vivo axonal damage exist, and studies of axonal ischemia and regeneration have largely relied on non-ischemic models such as optic nerve trauma (Kipnis et al., 2002, J. Neruoimmunol. 130, 78) optic nerve transection (Watanabe et al., 2001, Vis. Neurosci. 18, 137-145), and spinal cord trauma and transection (Shuman et al., 1997, J. Neurosci. Res. 50, 798-808; Beattie et al., 2002, Prog. Brain Res. 137, 37-47).

There is also a lack of models to study NAION, where it has been recognized in the art that occlusion does not mirror NAION infarcts of the ON (Tesser et al., 2003 Ophthalmology 110, 2031-2035). In order to study NAION, the inventor of the present invention has generated the first in-vivo model to analyze NAION: rodent anterior ischemic optic neuropathy (rAION). rAION closely resembles clinical NAION in many respects. Like NAION, rAION produces ON edema, and kills RGCs, by destroying RGC axons and oligodendrocytes comprising the ON. Similar to NAION, ON structures initially remain intact. The development of this experimental model has led to, for the first time, a precise characterization of the progression of ON-ischemic damage, identification of key components of early ischemia and quantification of treatment effectiveness. The rAION model has been extended to mice, enabling genetic analysis of ON-infarct sensitivity, evaluation of retinal and optic nerve gene expression patterns, and determination of the timing of post-infarct RGC death.

After evaluating 8 independent approaches for RGC preservation post-stroke, including estrogen, calcium channel blockers, glutamate inhibition, corticosteroid activation and herpes gene therapy, the inventor of the present invention has utilized gene array analysis to help identify potential gene changes that might suggest possible effective approaches. It was discovered that soon after ON stroke, there is up-regulation of previously unrecognized inflammatory responses that further compromise ON function. Post-infarct ON mRNA changes revealed that mRNA for inducible nitric oxide synthase (iNOS) was robustly upregulated one day post-infarct. There was also progressive decline in prostaglandin $D_2$ synthase ($PGD_2S$) over a three day period (see Table 1 and FIG. 1). Array analysis revealed that $PGD_2S$ levels declined, then rebounded dramatically around the time of ON edema resolution. Since iNOS is a major factor in CNS edema, a major function of prostaglandin $D_2$ is to inhibit iNOS activity, and $PGD_2$ metabolites are neuroprotective in trauma (Bernardo et al., 2000, Eur. J. Neruosci. 12, 2215-2223; Petrova et al., 1999, Proc. Natl. Acad. Sci. USA 96, 4668-4673), it was postulated by the present inventor that a derivative of the active $PGD_2$ metabolite, $PGJ_2$, could be neuroprotective following rAION. This was found to be true as discussed throughout the specification. Post-infarct administration of $PGJ_2$ (both systemic and intravitreal) reduced gross ON edema 1-3 days following rAION, with increased RGC survival.

These results identify a novel mechanism for neuroprotection, including without limitation early neuroprotection and reduction of edema in individuals suffering from NAION.

SUMMARY OF THE INVENTION

The inventor of the present invention describes a novel treatment for nerve injury and optic nerve diseases comprising administration of $PGJ_2$ to a subject in need thereof.

In one aspect, the present invention provides a method for reducing early onset of ON edema in a subject following infarction, comprising administering to a subject a therapeutically effective amount of $PGJ_2$.

In another aspect, the present invention provides a method for treating or reducing damage to an ON in a subject comprising administering to the subject a therapeutically effective amount of PGJ2.

In yet another aspect, the present invention provides a method for increasing RGC survival in a subject after injury comprising administering to a subject a therapeutically effective amount of $PGJ_2$.

In another aspect, the present invention provides a composition comprising $PGJ_2$, for increasing RGC survival after injury, for reducing early onset of optic nerve edema in a subject following infarction, and for treating or reducing nerve damage in a subject.

In yet another aspect, the present invention provides a composition comprising Granulocyte-Macrophage Colony Stimulating Factor (GM-CSF) for recruiting extrinsic macrophages into ON for increasing RGC survival and axonal regeneration and for stimulating degenerate myelin removal in a subject.

In still another aspect, the present invention provides a method for increasing RGC survival and axonal regeneration after ON damage, comprising administering to a subject a therapeutically effective amount of GM-CSF.

In yet another aspect, the present invention provides a composition for increasing RGC survival after ON damage in a subject, the composition comprising $PGJ_2$ and GM-CSF.

In still another aspect, the present invention provides a method for increasing RGC survival after ON damage in a subject, the method comprising administration of $PGJ_2$ and GM-CSF.

Preferably, the subject is a mammal, most preferably, a human.

The $PGJ_2$ may be administered, for example, systemically, or topically to the eye of the subject or by intraocular injection. The GM-CSF can be administered, for example, by stereotactic or intraventricular injection.

Various other features and advantages of the present invention are readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION

Figure 1:
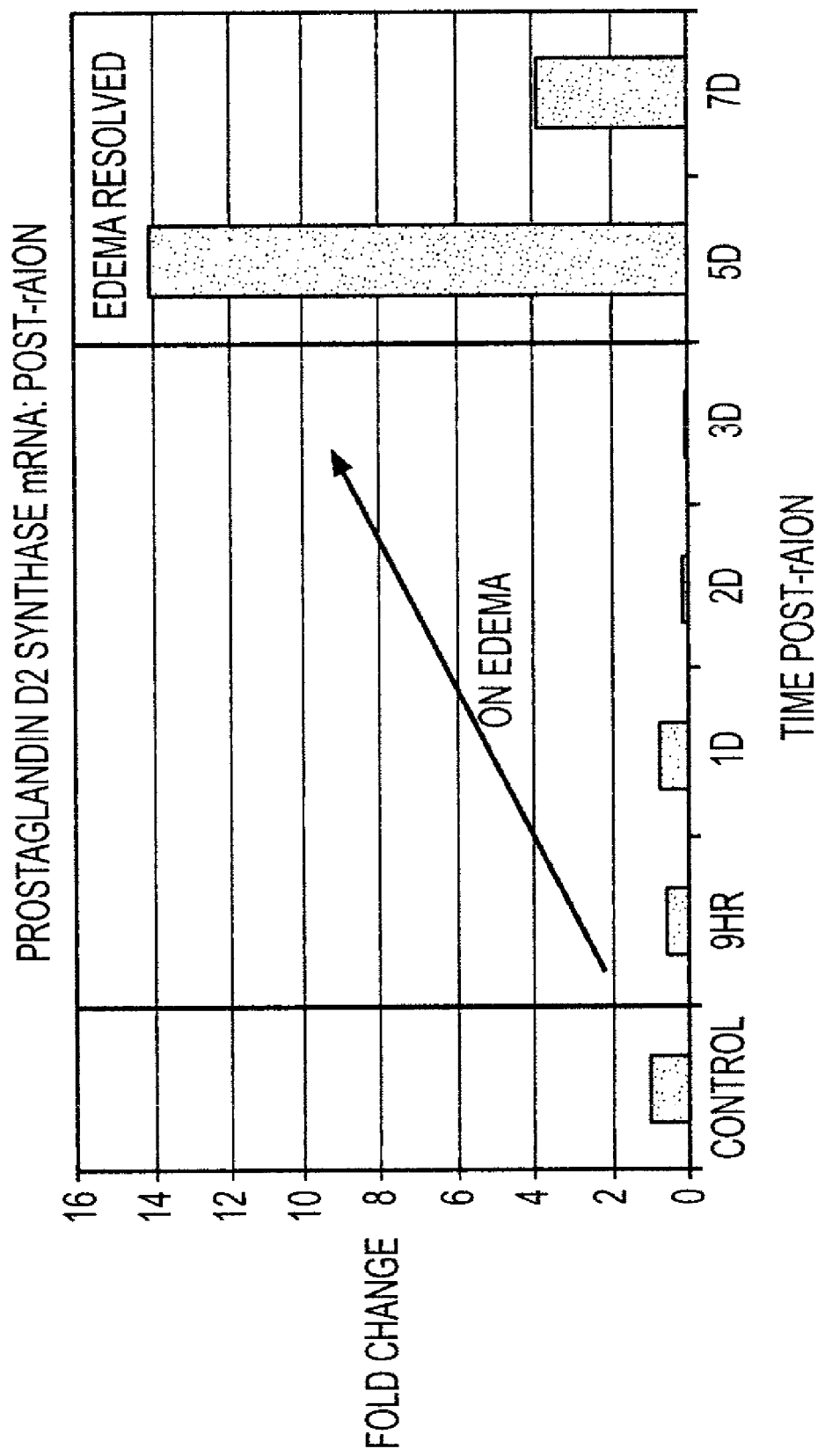
FIG. 1. RQ-PCR results of post-rAION prostaglandin D2 synthase mRNA levels in rat ON at different times. Three ONs from induced eyes were pooled for each assay point. Data was internally normalized for each set by utilizing cyclophilin B mRNA levels (for method see Goldenberg-Cohen, 2005, Invest. Opthalmol. Vis. Sci. 46, 2716-2725). Con: control (naïve ON). $PGD_2$ Synthase levels decline to 72% of control by 1 day, and even more (5% of control) by 3 days. There is a dramatic increase in $PGD_2$ Synthase at 5-7 days post-rAION, which corresponds to the time of edema resolution.

In certain embodiments, the present invention provides methods and compositions for treating or reducing damage or providing a neurosalutary effect to the ON, and more generally to a neuron, including damage resulting from ischemic or hypoxic stress, inflammation, excess intraocular pressure, or injury. The composition can be used specifically to treat damage associated with vascular occlusion or anterior ischemic optic neuropathy, and damage arising from the presence of cytotoxins or neurotoxins, such as glutamate or other excitatory amino acids or peptides, excess intracellular calcium, and free radicals. In particular, the composition can be useful in treating damage associated with branch and central vein/artery occlusion, trauma, edema, angle-closure glaucoma, open-angle glaucoma, age related macular degeneration, retinitis pigmentosa, retinal detachments, damage associated with laser therapy (including photodynamic therapy), and surgical light-induced iatrogenic retinopathy, ischemic optic neuropathy following intraocular surgery, post-traumatic optic neuropathy, and shock-induced ischemic optic neuropathy. The composition is also useful for treating specific genetic optic nerve diseases such as Lebers Hereditary optic neuropathy (LHON).

As used herein, a "neurosalutary effect" means a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The phrase "producing a neurosalutary effect" includes producing or effecting such a response or improvement in function or resilience within a component of the nervous system. Examples of producing a neurosalutary effect would include stimulating axonal outgrowth after injury to a neuron; rendering a neuron resistant to apoptosis; rendering a neuron resistant to a toxic compound such as ammonia, or other neurotoxins; reversing age-related neuronal atrophy or loss of function; or reversing age-related loss of cholinergic innervation.

As used herein, a prostaglandin J2, (PGJ$_2$), or "neurotrophic compound" or agent is one that induces a "neurosalutary effect" as defined above. Examples of neurotrophic compounds include PGJ$_2$; 15 deoxy delta 12,14 prostaglandin J2; and 9,10 dihydro-15-deoxy-delta 12,14 prostaglandin J2. In certain embodiments, 15 deoxy-delta 12,14 prostaglandin J2 is the form. Prostaglandin J2 is commercially available from Cayman chemical company, for example.

As used herein, GM-CSF is a neurotrophic agent which is capable of recruiting extrinsic macrophages to the ON after damage and stimulate degenerate myelin removal, and enhance RGC survival and axonal regeneration.

The composition may also include other factors that enhance the action of PGJ$_2$ or GM-CSF or benefit a neuron, including, for example, an axogenic factor. The term "axogenic factor" includes any factor that has the ability to stimulate axonal growth or regeneration of a neuron. Axogenic factors, include, for example, neurotrophin D1, and AF-1 (mannose) and AF-2 as described in, for example, Schwalb et al. (1996) Neuroscience 72, 901-10; Schwalb et al., id.; and U.S. Pat. No. 5,898,066, the contents of which are incorporated herein by reference. Other examples of axogenic factors include purines, such as inosine and other axogenic factors known to a person of skill in the art. In certain embodiments, the axogenic factor is mannose (e.g., D-mannose or L-mannose) or a mannose derivative, e.g., aminomannose, mannose-6-phosphate (Phosporic acid mano-(3,4,5,6-tetrahydroxy-tetrahydro-pyran-2-ylmethy) ester).

By "treat", "treating", "treated" or "treatment" it is meant any type of action that imparts a beneficial effect to a subject with a disease or illness encompassed by the present invention, including improvement in the condition of the subject (e.g., in one or more symptoms), delay in the progression of the condition, prevention or delay in the onset of the disorder, and/or change in clinical parameters, disease or illness, etc., as would be well known in the art.

A therapeutically effective amount or dosage of an axogenic factor may range from about 0.001 to 30 mg/kg body weight, with other ranges of the invention including about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, and 5 to 6 mg/kg body weight. For inosine, a non-limiting range for a therapeutically effective in vivo concentration in tissue containing the injury is 5 uM to 5 mM.

The term "administering" to a subject includes dispensing, delivering or applying an active compound in a pharmaceutical formulation to a subject by any suitable route for delivery of the active compound to the desired location in the subject, including delivery by, for example, either the parenteral or oral route, stereotactic injection, intraocular, intravitreal, intraventricular injection, intramuscular injection, subcutaneous/intradermal injection, intravenous injection, buccal administration, transdermal delivery and administration by the rectal, colonic, vaginal, intranasal or respiratory tract route.

By the term "co-administer" is intended that at least two of the components of the active compound be administered during a time frame wherein the respective periods of biological activity overlap. Thus the term includes sequential as well as coextensive administration of the components of the active compound of the present invention.

As used herein, the language "contacting" is intended to include both in vivo or in vitro methods of bringing a compound of the invention into proximity with a neuron such that the compound can exert a neurosalutary effect on the neuron.

As used herein, the term "effective amount" includes an amount effective, at dosages and for periods of time necessary, to achieve the desired result, such as sufficient to produce a neurosalutary effect in a subject. An effective amount of an active compound as defined herein may vary according to factors such as the disease state, age, and weight of the subject, and the ability of the active compound to elicit a desired response in the subject. Dosage regimens may be adjusted to provide the optimum therapeutic response. An effective amount is also one in which any toxic or detrimental effects of the active compound are outweighed by the therapeutically beneficial effects.

The term "damage" is intended to include deleterious or abnormal alterations in a cell homeostasis, function, or survivability. In particular embodiments, the cell is a nerve cell.

The term "damage" is also intended to encompass cell death through necrosis, apoptosis, or other mechanisms of cell death. Additionally, the term includes both reversible and irreversible damage.

The term "subject" is intended to include animals. In particular embodiments, the subject is a mammal, including, for example, a human, a nonhuman primate, a dog, a cat, a horse, a cow and other domestic and commercially important animals in need of treatment for damage to the nervous system including, but not limited to, damage to white matter, an ON, RGCs, and other cell bodies or neurons of the nervous system. A subject of the invention can also include a subject not previously known or suspected to have NAION, i.e. prophylactically. A subject of this invention is also a subject known or believed to be at risk of damage to the nervous system. This includes individuals who are about to undergo major circulation-changing surgery that will put stress on the optic nerve, including, for example, cardiac surgery, spinal surgery and brain surgery.

The route of administration and the dosage regimen will be determined by skilled clinicians, based on factors such as the exact nature of the condition being treated, the severity of the condition, and the age and general physical condition of the patient. Specific routes of administration may include topical application (such as by eyedrops, creams or erodible formulations to be placed under the eyelid), intraocular injection into the aqueous or the vitreous humor, injection into the external layers of the eye, such as via subconjunctival injection or subtenon injection, parenteral administration or via oral routes.

The neurotrophic compound or agent PGJ$_2$ or GM-CSF may be contained in various types of pharmaceutical compositions, in accordance with formulation techniques known to those skilled in the art. For example, the compounds may be included in tablets, capsules, solutions, suspensions, and other dosage forms adapted for oral administration; solutions and suspensions adapted for parenteral use; and solutions and suspensions adapted for topical ophthalmic, depot, or intraocular injection, stereotactic injection, or intraventricular injection. Solutions, suspensions, and other dosage forms adapted for depot or intra-ocular injection are particularly preferred for the prevention or treatment of acute or chronic retinal or optic nerve damage.

The present invention is particularly directed to compositions adapted for treatment of optic nerve cells or tissues. The composition may contain additives such as preservatives, wetting agents, emulsifying agents, dispersing agents and the like. The ophthalmic compositions of the present invention will include PGJ$_2$ and/or GM-CSF, alone or in combination, and a pharmaceutically acceptable vehicle. An axogenic factor may also be included in the composition.

Various types of vehicles may be used. Vehicles for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates.

The vehicles will generally be aqueous in nature. Aqueous solutions are generally preferred based on ease of formulation as well as a patient's ability to easily administer such compositions by means of instilling one to two drops of the solutions in the affected eyes. However, the $PGJ_2$ and/or GM-CSF of the present invention may also be readily incorporated into other types of compositions, such as suspensions, viscous or semi-viscous gels, or other types of solid or semi-solid compositions. Suspensions may be preferred for neurotrophic compounds or agents that are relatively insoluble in water. The ophthalmic compositions of the present invention may also include various other ingredients, such as buffers, preservatives, co-solvents, and viscosity building agents.

An appropriate buffer system (e.g., sodium phosphate, sodium acetate or sodium borate) may be added to prevent pH drift under storage conditions.

Ophthalmic products for topical use may be packaged in multidose form. Preservatives are thus required to prevent microbial contamination during use. Suitable preservatives include: for example, benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v"). Such preparations may be packaged in dropper bottles or tubes suitable for safe administration to the eye, along with instructions for use.

The preservatives of the present invention may also contain pharmaceutically acceptable antifungal acids such as boric acid; benzoic acid; salicylic acid; sorbic acid; lactic acid; acetic acid; and pharmaceutically acceptable salts thereof. The antifungal acid component can be added to pharmaceutical compositions in the form of a pharmaceutically acceptable salt.

The ophthalmic composition can optionally include a demulcent. Demulcents are substances that soothe irritated tissue, particularly mucous membranes. Demulcents (or humectants) are used for lubricating mucous membrane surfaces and for relieving dryness and irritation. The term "demulcent", as used herein is intended to mean an agent, usually a water-soluble polymer, which is applied topically to the eye to protect and lubricate mucous membrane surfaces and relieve dryness and irritation. Within this meaning, the term "wetting agent" is also commonly used. Furthermore, it will be understood that some constituents possess several functional attributes. For example, cellulose derivatives are common demulcents, but are also used as "viscosity increasing agents". Similarly, glycerin is a known demulcent but is also used as a "tonicity adjusting agent". Examples of the most widely used demulcents include: polyvinyl alcohol, polyvinyl pyrrolidone, cellulose derivatives and polyethylene glycol.

The present invention may also contain suspending agents (e.g., polyvinylpyrrolidone, glycerin monostearate) and dispersing agents (e.g., surfactants such as tyloxapol and polysorbate, ionic polymers such as sodium alginate) in addition to the additives listed above, whereby ensuring that the eye drop formulation is a further uniform microparticulate and satisfactorily dispersed aqueous suspension.

When the ophthalmic compositions of the present invention are administered during intraocular surgical procedures, such as through retrobulbar or periocular injection and intraocular perfusion or injection, the use of balanced salt irrigating solutions as vehicles are most preferred. BSS Sterile Irrigating Solution and Sterile Intraocular Irrigating Solution (Alcon Laboratories, Inc., Fort Worth, Tex. USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, Ophthalmic Surgery: Principles of Practice, Ed., G. L. Spaeth. W. B. Sanders Co., Philadelphia, Pa., U.S.A., (1990).

As indicated above, use of the ophthalmic compositions of the present invention to treat or reduce damage to, for example, retinal and optic nerve tissues, as well as to enhance functional recovery after damage to, for example, ocular tissues, is an aspect of the present invention. Ophthalmic conditions that may be treated include, but are not limited to, retinopathies (including diabetic retinopathy and retrolental fibroplasia), macular degeneration, ocular ischemia, and glaucoma. Other conditions to be treated with the methods of the invention include, for example, damage associated with injuries to ophthalmic tissues, such as ischemia reperfusion injuries, photochemical injuries, and injuries associated with ocular surgery, particularly injuries to the retina or optic nerve by exposure to light or surgical instruments. The ophthalmic compositions may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The ophthalmic compositions may also be used prophylactically, especially prior to ocular surgery or noninvasive ophthalmic procedures or other types of surgery.

In general, the doses used for the above described purposes will vary, but will be in an effective amount to treat, reduce or ameliorate retinal or optic nerve cell or tissue damage resulting from any of the above listed conditions. As used herein, the term "therapeutically effective amount" refers to an amount of $PGJ_2$ and/or GM-CSF, alone or in combination, or other compositions, compounds, or agents of the invention, such that treatment of a patient with that amount can be associated with a medically desirable change in ocular function, or that can treat, reduce, or ameliorate chronic or acute damage as described throughout the specification, or as would be known by one of ordinary skill in the art, including, for example, nervous system cell or tissue damage, ON damage, RGC damage, and white matter damage, resulting from conditions such as, for example, ischemia to an optic nerve, optic nerve stroke, NAION, trauma to the eye, ischemia or hypoxia.

The doses used for any of the above-described purposes of the $PGJ_2$ and/or GM-CSF will generally be from about 0.01 to about 100 milligrams per kilogram of body weight (mg/kg), administered one to four times per day. Other dosages used for any of the above-described purposes include about 0.1 to 90 mg/kg body weight, about 1.0 to 80 mg/kg body weight, about 2.0 to 70 mg/kg, about 3.0 to 60 mg/kg, about 4.0 to 50 mg/kg, about 5.0 to 40 mg/kg, about 6.0 to 30 mg/kg, about 7.0 to 20 mg/kg body weight, and about 8.0 to 10 mg/kg body weight of $PGJ_2$ and/or GM-CSF. In one embodiment of the invention, a therapeutically effective amount of the composition is from about 99.0 to about 101.0 milligrams per kilogram of body weight (mg/kg), administered one to four times per day. When the compositions are dosed topically, they will generally be in a concentration range of from 0.001 to about 5% w/v, with 1-2 drops administered 1-4 times per day. Other with other ranges of the invention including from 0.01 to about 4% w/v, from 0.1 to about 3% w/v, from 1.0 to about 2% w/v, with 1-2 drops administered 1-4 times per day.

There is also provided an article of manufacture comprising packaging material and a pharmaceutical agent contained within the packaging material. The packaging material comprises a label which indicates that the pharmaceutical may be administered, for a sufficient term at an effective dose, for treating damage to the retina and optic nerve, including, for example, damage resulting from ischemic or hypoxic stress, excess intraocular pressure, or injury, or damage resulting from glaucoma and macular degeneration. The pharmaceutical agent comprises neurotrophic compounds or agents of the present invention together with a pharmaceutically acceptable carrier.

As used herein, the term "pharmaceutically acceptable carrier" refers to any formulation which is safe, and provides the appropriate delivery for the desired route of administration of an effective amount of at least one compound of the present invention.

Pharmaceutical compositions (also referred to herein as "ophthalmic compositions") that comprise a $PGJ_2$ and/or GM-CSF, alone or in combination, and a pharmaceutically acceptable carrier may be packed with instructions for use of the pharmaceutical composition for treatment of damage to the retina or optic nerve. In one embodiment, the pharmaceutical composition may further include an axogenic factor, such as AF-1, AF-2 or a purine such as inosine. The ingredients may be packaged together in the form of a kit.

All of the components, e.g., $PGJ_2$ and/or GM-CSF, and/or an axogenic factor, can be used separately, but administered contemporaneously, and can be given via a singular pharmaceutically acceptable dosage form for each component or combination of all the components as an immediate release or controlled release dosage form. Contemporaneously means the agents are administered separately over time, but have a combined effect together after their individual administrations.

All publications, including, but not limited to patents and patent applications, cited in this specification are herein incorporated by reference as if each individual publication were specifically and individually indicated to be incorporated by reference herein as though fully set forth.

The invention is further described in detail to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided therein.

EXAMPLES

Example 1

Using the rAION Model to Evaluate Protection Strategies rAION-associated cell loss is analyzed using stereological analysis. Stereology incorporates statistically valid methods of quantitative cellular analysis (Schmitz, 2005, Neuroscience 130, 813-831) and is the current state of the art for evaluating quantitative changes in cell numbers in a given tissue. Rat RGC identification is performed using retrograde fluorogold labeling via superior colliculus injection of 2% (3 ul/side) fluorogold, or more recently, utilizing either Bex-½ or Brn3a immunostaining of rat retina (Bernstein et al., 2006, Mol. Vis. 12, 147-155; Bernstein et al., 2007, Invest. Opthalmol. Vis. Sci. 48, 2304-2310; Weishaupt et al., 2005, J. Mol. Neurosci 26, 17-26). Brn3a immunolabeling identifies >86, 000 RGCs in flat-mounted whole retinae (Yaacobi et al, 2007, Invest. Opthalmol. Vis. Sci. 45 (suppl)).

Example 2

Gene Expression Studies in rAION and ONArray Analysis

Gene array analysis was utilized to identify potential gene changes that might suggest possible effective therapeutic approaches. Data from gene array experiments revealed strong up-regulation of inflammation-associated genes, including TNFR1, Mx3 (an interferon response protein that plays a major role in increasing cellular inflammation) and suppressor of cytokines-3 (SOCS-3), both of which act via the Jak/Stat pathway. Additionally, a number of cytokines or cytokine-regulating proteins are up-regulated early (1-3d) in rAION-induced tissue, suggesting an attempt to regulate specific inflammatory pathways activated after ON stroke. Oncomodulin (an extrinsic macrophage-derived protein that enhances RGC axonal regeneration) {Yin et al., 2006, Nat. Neurosci. 9, 843-852) is present only at very low retinal levels in both control and post-rAION induced retina. Osteopontin (a macrophage/microglial induced protein that blocks axonal growth) increases significantly at 3 days post-infarct. These findings confirm that CNS axonal infarction is associated with inflammation-related mechanisms that block, rather than enhance, axonal regrowth. Importantly, inducible nitric oxide synthase (iNOS), increases significantly (2.55 fold) in the retina within a single day (Table 1). Quantitative real time PCR (rq-PCR) of mRNA derived from ON reveals dramatic early changes in iNOS mRNA levels (14 fold increase by 9 hours). There is an early (1-3 day) post-rAION decline in retinal-$PGD_2$ synthase mRNA.

TABLE 1

Table 1. Microarray analysis: Expression of a subset of inflammation- and retina-expressed genes following rAION induction.

| L1 | L3 | R1 | R3 | R1/L1 | R3/L3 | Accession | Description |
|---|---|---|---|---|---|---|---|
| Inflammation | | | | | | | |
| 119.35 | 110.25 | 506.65 | 112.6 | 4.24 | 1.02 | M63122 | tumor necrosis factor receptor (TNFR1) |
| 103.1 | 53.1 | 253.85 | 72.85 | 2.46 | 1.37 | AF075383 | SOCS-3 |
| 190 | 162.65 | 387.4 | 196.85 | 2.03 | 1.21 | AF065161 | cytokine-inducible protein |
| 570.7 | 1094 | 2015 | 1003 | 3.53 | 0.91 | X61381 | interferon induced mRNA |
| 31.55 | 20.55 | 34.05 | 31.5 | 1.07 | 1.53 | L00981 | tumor necrosis factor (TNF-alpha) gene |
| 263.4 | 233.45 | 672.85 | 310.15 | 2.55 | 1.32 | U16359 | inducible Nitric Oxide Synth. (iNOS) |

TABLE 1-continued

Table 1. Microarray analysis: Expression of a subset of inflammation- and retina-expressed genes following rAION induction.

| L1 | L3 | R1 | R3 | R1/L1 | R3/L3 | Accession | Description |
|---|---|---|---|---|---|---|---|
| 1879.1 | 2459 | 1728 | 1808 | 0.92 | 0.73 | J04488 | Prostaglandin D2 Synthase |
| 26.3 | 29.35 | 17.6 | 42.45 | 0.67 | 1.45 | J02705 | Oncomodulin |
| 214.55 | 151.35 | 395.1 | 519.45 | 1.84 | 3.43 | M14656 | Osteopontin |
| Glial function | | | | | | | |
| 844.3 | 10.49 | 3845 | 3641 | 4.55 | 3.46 | AF028784 | GFAP, alternative spliced form, complete |
| Photoreceptor function | | | | | | | |
| 5344 | 5080.7 | 4209.2 | 4180 | 0.78 | 0.83 | L02634 | cGIMP-gated rod photoreceptor channel |
| 3431.75 | 3044.6 | 29.38 | 28.26 | 0.85 | 0.92 | U63971 | rhodopsin kineae |
| 39678 | 43576 | 33980 | 45108 | 0.95 | 1.03 | Z46957 | rhodopsin |
| Retinal ganglion cell specific or enriched function | | | | | | | |
| 737.5 | 766.85 | 627.3 | 552.1 | 0.85 | 0.73 | M31178 | Calbindin D28 |
| 991.15 | 1217.3 | 706.2 | 637.6 | 0.71 | 0.52 | U88958 | Neuritin mRNA |
| 865.6 | 739.3 | 672.25 | 585.2 | 0.78 | 0.79 | X02002 | Thy-1 gene for cell-surface glycoprotein |
| 5402 | 4850 | 4261 | 3804 | 0.79 | 0.78 | AB003991 | SNAP-25A |
| 1755 | 1757 | 1594 | 1520 | 0.91 | 0.86 | L25633 | Neuroendocrine-specific protein (RESP18) |

Data from 3 affymetrix U34A rat chips. Pooled retinal RNA from three eyes (male) per chip; total = 9 animals for three chips for each condition) were rAION induced. Tissue was collected 1 and 3 days post-induction. Retinal RNA was extracted from 1- and 3-day controls (L1 and L3) and 1- and 3 days induced (R1 and R3) eyes for both sets. Average signal values (3 chips/condition) shown for each group. Four clusters are shown (inflammation, glial function, photoreceptor and retinal ganglion cell function), determined by both Genespring software, and historical references.
Average values with statistically significant changes (p < 0.05), compared between 1d or 3d left eyes (controls) and experimental (rAION) eyes are shown in bold.

Example 3

PGD$_2$ Pathway Activation is Neuroprotective after ON Infarct

Post-infarct ON mRNA changes revealed that mRNA for inducible nitric oxide synthase (iNOS) was robustly upregulated 1d post-infarct (see Table 1). There was also progressive decline in prostaglandin D$_2$ synthase (PGD$_2$S) over a three day period (Table 1). Rq-PCR revealed that PGD$_2$S levels declined, then rebounded dramatically around the time of ON edema resolution. Since iNOS is a major factor in CNS edema, a major function of prostaglandin D$_2$ is to inhibit iNOS activity, and PGD$_2$ metabolites are neuroprotective in trauma (Bernardo et al., 2000, Eur. J. Neurosci. 12, 2215-2223; Petrova et al., 1999, PNAS USA 96, 4668-4673).

The inventors of the present invention interpreted this to suggest that ON infarction results in early ON-PGD$_2$ synthase downregulation, and decreased PGD$_2$ metabolites, exacerbating ON edema. Since PGD$_2$'s major metabolite (PGJ$_2$) is highly neuroprotective (Giri et al., 2004, J. Immunol. 173, 5196-5208; Lin et al., 2006, Arterioscler. Thromb. Vasc. Biol. 26, 481-487) and plays a major role in regulating inflammatory damage via iNOS {Bernardo, 2003, supra; Giri, 2004, supra), the inventors next evaluated whether or not early post-infarct PGD$_2$ down-regulation exacerbates ON edema by enabling increased iNOS expression. Increased iNOS activity increases NO production, resulting in additional ON edema and ON damage.

Figure 2:
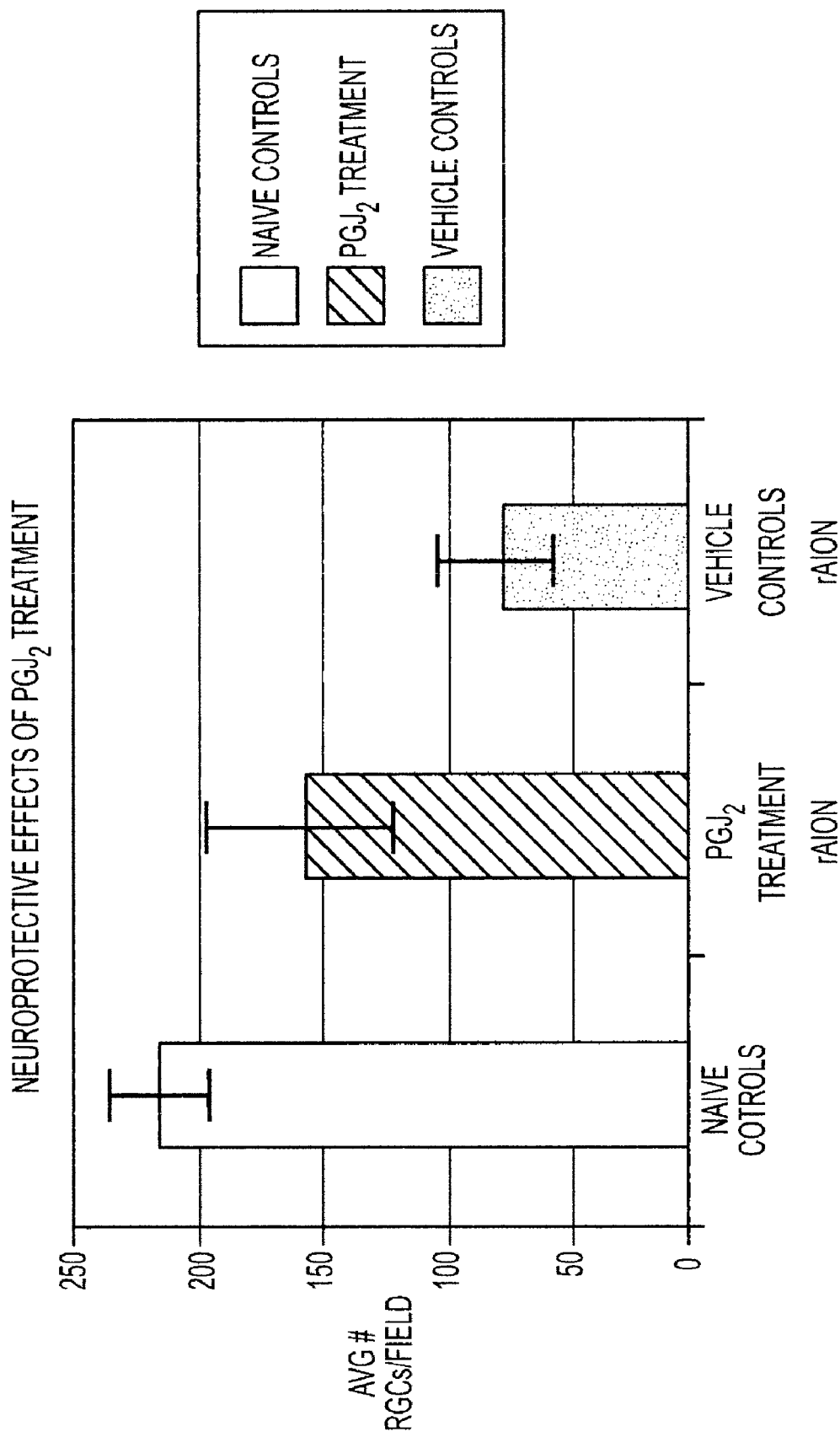
FIG. 2. Stereological analysis of RGC numbers in naïve and rAION induced rat retinae treated with either $PGJ_2$ or Vehicle (PBS). Animals were injected IV 1Xd for 3 days with either 100 mg/kg $PGJ_2$ or PBS-vehicle. Animals were euthanized and retinae analyzed 30 days post-rAION induction. Average numbers based on 4 retinae/group; RGC stereology derived from Brn3a (+) RGC immunostaining.

The data presented herein shows that post infarct administration of PGJ$_2$ (both systemic and intravitreal) for the first 3 days post-induction reduces ON edema (by direct fundus observation in the living animal) 1-3 days following rAION. PGJ$_2$-treated animals have increased RGC survival 30 days post-rAION induction (FIG. 2). PGJ$_2$-treated animals have 72.4% of the number of naïve RGCs compared with 34.3 for vehicle treated animals (black bar, FIG. 2).

Example 4

PGJ2-Associated Edema Reduction

Figure 3:
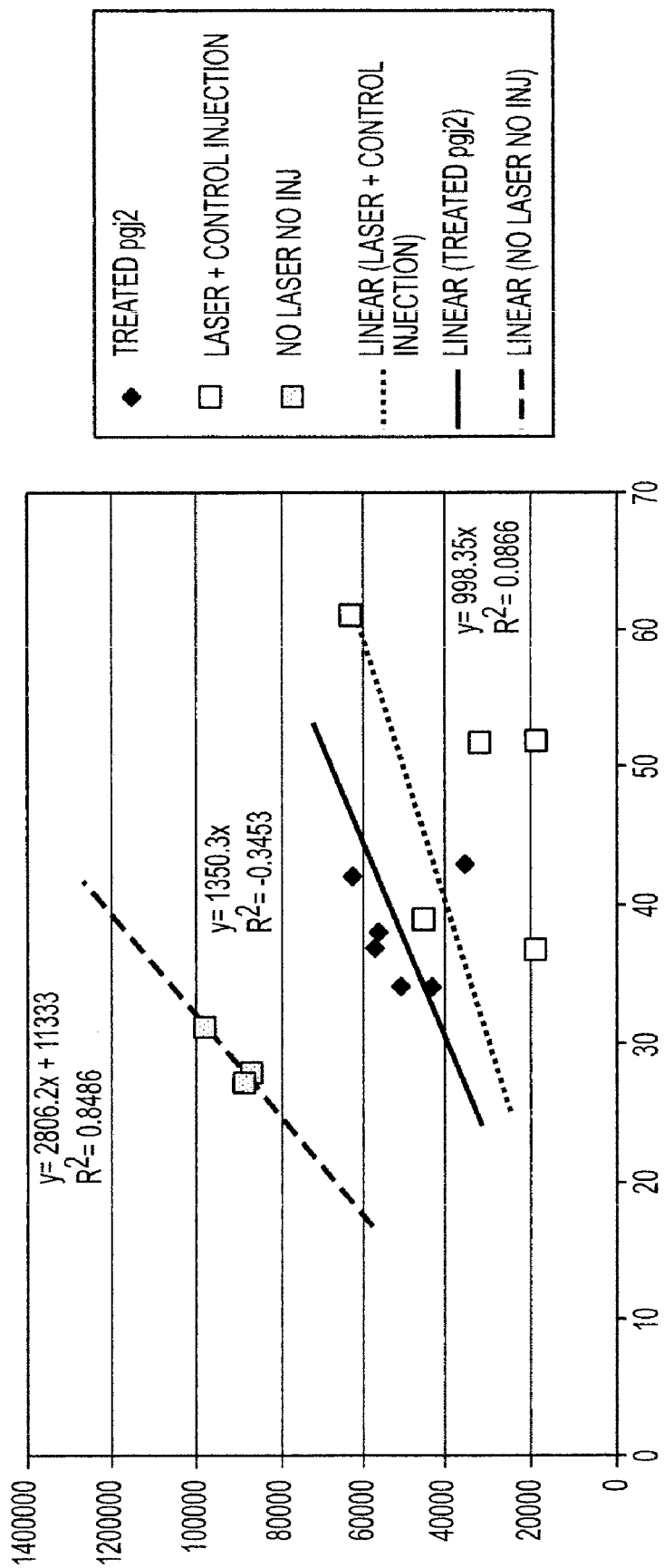
FIG. 3. Statistical analysis of 15-deoxy delta (12,14) $PGJ_2$ administration to rats after optic nerve (ON) stroke. ON stroke was administered to a 75% predicted loss of retinal ganglion cell loss by the method of Bernstein et al, Invest. Ophth. Vis. Sci. 2003, 44, 4153-4162. The ordinate represents the number of retinal ganglion cells in each retina. The abscissa represents the number of fields of cells counted to reach a statistically valid number as determined by the field of stereology. The green line represents the typical number of retinal ganglion cells in the untreated (naïve; no stroke) rat retina. The response of rat retina and optic nerve to vehicle treatment is shown in yellow. The response of PGJ2 treated animals is shown in Blue. There is a 35-50% preservation of the neurons whose axons comprise the optic nerve, in animals who have received ON stroke and then received $PGJ_2$ treatment.

Since PGD$_2$'s major metabolite PGJ$_2$ is highly neuroprotective and plays a major role in regulating inflammatory damage via iNOS, without being bound by theory it is believed that addition of the active PGD$_2$ metabolite PGJ$_2$ will reduce iNOS expression, resulting in reduced NO production, reduced ON edema and reduced retina and optic nerve damage. Rats were used for this experiment and ON stroke was administered to a 75% predicted loss of RGCs by the method of Bernstein et al., 2003, supra. RGC's were counted in each retina in the untreated (naïve; no stroke) and rats with rAION treated with PGJ$_2$. Results indicate that there is a 35-50% preservation of the neurons whose axons comprise the optic nerve in animals that underwent ON stroke and then received PGJ$_2$ treatment (FIG. 3).

Example 5

GM-CSF for Recruitment of Extrinsic Macrophages

The present inventor has identified significant, but subtle early macrophage activation after optic nerve infarct. Post-infarct CNS inflammation occurs in white matter (lacunar) infarcts, and post-stroke inflammatory modulation of white matter has been proposed as a treatment approach (Castellanos et al., 2002, Stroke 33, 982-987). It is logical to assume that since the ON is a part of the CNS, ON responses are likely to be similar to that seen in other CNS (white matter) regions. Cellular inflammation exerts both considerable beneficial and detrimental effects following CNS infarct (Anderson, 2002, J. Spinal Cord. Med. 25, 70-79).

Granulocyte-Macrophage Colony Stimulating Factor (GM-CSF) directly activates macrophages, and has been utilized to obtain external (as opposed to intrinsic) macrophages in a given region (Nishijima et al., 1997, Blood 90, 1031-1038; Love, 2003, Lancet Neuro. 2, 458; Ousman and David, 2001, J. Neurosci. 21, 4649-4656). GM-CSF increases macrophage mitosis, in addition to recruiting external macrophages, by activation (through phosphorylation) of the Janus kinase-signal transduction and transcription (Jak/STAT) factor members STAT6, 5A and STAT3 (Feldman et al., 1997, Blood 90, 1768-1776; Potts et al., 1998, Dev. Biol. 204, 277-292). By increasing local cellular inflammation through 'vaccination', or activating macrophages and T cells against myelin components after optic nerve trauma or ischemia, external macrophage addition, or attraction of extrinsic macrophages by GM-CSF administration (Buschmann et al., 2003, Circulation, 108, 610-615), a measure of RGC and other CNS rescue can be achieved, suggesting that, rather that simply being toxic, enhancing post-ischemic inflammation can be beneficial.

The present inventor has evaluated the location of early ON-macrophage activity following rAION induction, using antibodies for both general cellular inflammation (IBA-1) and extrinsic macrophages (detected by antibody to ED-1). Results reveal that GM-CSF has the ability to recruit extrinsic macrophages (data not shown). Few, if any extrinsic macrophages are present in normal uninfarcted ON (results not shown). Following rAION induction, ED-1(+) extrinsic macrophages enter the ON and cluster in the primary ischemic lesion site immediately behind the retina/ON junction. Little extrinsic macrophage infiltration occurs >250 microns post-ON/retina junction. Extrinsic infiltration does not extend beyond the primary lesional site, and decreases rapidly over a two-week period of time. By 6 days post-induction, there are decreased numbers of ED-1(+) cells in an animal treated with 1 ug of GM-CSF stereotactically injected into the superior colliculus. Control (vehicle treated animals) show a similar pattern (data not shown). This reveals that GM-CSF is not retrograde axonally transported by RGC axons (at least by 3 days post-injection in intact axons close to the primary lesion site). However, intraventricular GM-CSF injection results in significantly enhanced recruitment of ED-1(+) cells in rAION-induced ONs (data not shown). Extrinsic macrophages extend beyond the initial lesion site, even during early axonal degeneration occurring 6 days post-induction. Thus, it is possible to administer intraventricular GM-CSF to recruit extrinsic macrophages into the ON following rAION, and determine whether the macrophage recruitment approach is useful to enhancing ON-axonal repair and regeneration following ON infarct.

Results confirm that, while previously unsuspected, significant early inflammation accompanies rAION to control ON. Cellular inflammation associated with extrinsic macrophages invade near the primary lesion, but further downstream in the ON, CD68 (+)/ED1(−) macrophages predominate. This staining pattern is typical of microglia. Thus, the cellular inflammation occurring downstream from the primary lesion consists of activation of resident microglia, not infiltration of extrinsic macrophages. Since extrinsic macrophages enhance axonal regeneration, and not resident microglia, this implies that any axonal regeneration effort is likely to be abortive; stopping at the extrinsic inflammation border. In fact, this is exactly what happens. Using a GAP43 signal (a marker of axonal regeneration) we determined that the signal never gets past the primary lesion site (data not shown).

Therefore, despite early inflammation, extrinsic macrophages cannot migrate through the ON distal to the primary lesion, and this is coupled by a relatively rapid decline of cellular inflammation through the ON. Therefore, without additional enhancement of extrinsic macrophage recruitment, extrinsic macrophage recruitment and infiltration only occurs close to the rAION-induced primary lesion (the ON-retina junction). Distal to the primary lesion, resident macrophages are eventually activated, then slowly decline in activity.

Since extrinsic macrophages are responsible for removing myelin and enhancing RGC survival, early post-infarct inflammatory changes are only sufficient to remove myelin near the retina/ON junction, but insufficient to maintain extrinsic macrophage migration, clear degenerate myelin, and repair and stimulate axonal regeneration via oncomodulin secretion. This is an inability to effectively remove axonal regrowth-inhibitory myelin and remodel the ON following optic nerve stroke. administration of GM-CSF will result in recruitment of additional extrinsic macrophages into the post-infarcted optic nerve thereby stimulating degenerate myelin removal, and enhancing RGC survival and axonal regeneration.

What is claimed is:

1. A method of treating non-arteritic ischemic optic neuropathy (NAION) in a subject, comprising administering to the subject a therapeutically effective amount of a composition comprising prostaglandin J2, thereby treating the non-arteritic ischemic neuropathy (NAION) in the subject.

2. The method of claim 1, wherein the composition is administered topically or intraocularly.

3. The method of claim 1, wherein the therapeutically effective amount of the composition is from about 99.0 to about 101.0 milligrams per kilogram of body weight (mg/kg), administered one to four times per day.

4. The method of claim 1, wherein the composition is administered intravitreally.

5. The method of claim 4, wherein the administered amount of the composition is from about 10 to about 100 micrograms per kilogram of body weight (μg/kg).

6. The method of claim 1, wherein the administered amount of the composition is from about 10 to about 100 micrograms per kilogram of body weight (μg/kg).

* * * * *